US008178088B2

(12) United States Patent
Julien

(10) Patent No.: US 8,178,088 B2
(45) Date of Patent: *May 15, 2012

(54) ANTIPROTOZOAL COMPOSITION

(75) Inventor: William E. Julien, Omaha, NE (US)

(73) Assignee: Church & Dwight Co., Inc., Princeton, NJ (US)

( * ) Notice: Subject to any disclaimer, the term of this patent is extended or adjusted under 35 U.S.C. 154(b) by 1332 days.

This patent is subject to a terminal disclaimer.

(21) Appl. No.: 11/391,188

(22) Filed: Mar. 28, 2006

(65) Prior Publication Data

US 2006/0193834 A1 Aug. 31, 2006

Related U.S. Application Data

(60) Division of application No. 10/151,126, filed on May 18, 2002, now abandoned, which is a continuation-in-part of application No. 08/688,955, filed on Jul. 31, 1996, now abandoned.

(51) Int. Cl.

| | |
|---|---|
| ***A23G 3/00*** | (2006.01) |
| ***A23K 1/00*** | (2006.01) |
| ***A23L 1/20*** | (2006.01) |
| ***A01N 63/00*** | (2006.01) |
| ***B65B 29/02*** | (2006.01) |
| ***C12N 1/12*** | (2006.01) |
| ***C12N 1/20*** | (2006.01) |

(52) U.S. Cl. ......... 424/93.4; 426/78; 426/630; 426/635; 426/658; 426/807; 435/252.1; 435/843

(58) Field of Classification Search ........................ None
See application file for complete search history.

(56) References Cited

U.S. PATENT DOCUMENTS

| | | | | | |
|---|---|---|---|---|---|
| 2,700,611 | A * | 1/1955 | Jeffreys | .......................... | 426/71 |
| 3,308,035 | A * | 3/1967 | Douros, Jr. | ......................... | 426/7 |
| 3,732,144 | A * | 5/1973 | Nakayama et al. | ........... | 435/115 |
| 3,821,416 | A * | 6/1974 | Thompson et al. | ............... | 426/2 |
| 3,862,333 | A * | 1/1975 | Chalupa et al. | ............... | 514/754 |
| 4,145,445 | A * | 3/1979 | Hitzman | .......................... | 426/60 |
| 4,209,590 | A * | 6/1980 | MacFadden | .................. | 435/244 |
| 5,498,532 | A * | 3/1996 | Katsumata et al. | ........... | 435/106 |
| 5,709,894 | A * | 1/1998 | Julien | ............................. | 426/53 |
| 5,783,238 | A * | 7/1998 | Julien | ............................. | 426/63 |
| 5,861,162 | A * | 1/1999 | Nagaraja et al. | ........... | 424/203.1 |
| 5,863,574 | A * | 1/1999 | Julien | ............................. | 426/53 |
| 6,312,710 | B1 * | 11/2001 | Julien | ........................... | 424/438 |

FOREIGN PATENT DOCUMENTS

WO 98/04283 * 2/1998

* cited by examiner

*Primary Examiner* — Debbie K Ware

(74) *Attorney, Agent, or Firm* — Frenkel & Associates, P.C.; Stephen B. Shear

(57) ABSTRACT

A composition, and method of use, for controlling, reducing or preventing the growth of protozoal bacteria in the rumen of a ruminant comprising cell bodies of a facultative anaerobe selected from the group consisting of *Corynebacterium* cell bodies and *Brevibacterium* cell bodies or a mixture of *Corynebacterium* cell bodies and *Brevibacterium* cell bodies, glutamic acid fermentation solubles, corn fermentation solubles, glutamic acid fermentation solubles and corn fermentation solubles.

2 Claims, No Drawings

ANTIPROTOZOAL COMPOSITION

CROSS REFERENCE TO RELATED APPLICATIONS

This Application is a Divisional of application Ser. No. 10/151,126, filed May 18, 2002, now abandoned, which is a Continuation-In-Part of application Ser. No. 08/688,955, filed Jul. 31, 1996, now abandoned.

STATEMENT REGARDING FEDERALLY SPONSORED RESEARCH OR DEVELOPMENT: N/A

BACKGROUND OF THE INVENTION

The invention relates to a method of using a composition and compound with antiprotozoal activity. These methods and materials will potentiate control of protozoal populations under a variety of conditions, particularly in ruminants.

The normal diet of the ruminant animal is forage. Forage includes grasses, legumes and cellulytic byproducts of agricultural production. These are either fed fresh as pasture or green chop; in a dry form as hay; or in a preserved state as silage. The ability to utilize these materials as sources of nutrients is only possible as a result of pregastric bacterial fermentation in the rumen, the nonfundic portion of the animal's stomach. Here, bacterial action reduces the complex structural carbohydrates; cellulose, hemicellulose, and lignin and the associated nonstructural carbohydrates; pectin, starches and sugars, to either fatty acids or more chemically simplistic carbohydrate forms, which are then subjected to gastric action in the fundic stomach and small intestine.

The adaptation of ruminants to pregastric digestion has involved a system of retention of digesta, which is an essential part of the mechanism for maximal extraction of energy. This retention requires some sacrifices in food intake, which becomes more limited on forage based diets because the coarser ingests must be retained longer to achieve efficient extraction of energy. This poses a special problem in the modern, domesticated ruminant, in that the nutrient demands created by genetic selection for rapid lean muscle growth or high levels of milk production far exceed the supply generated by rumenal fermentation of forage based diets.

The diets that must be fed require the addition of large amounts of nonstructural carbohydrate (starches and sugars) fed in the form of grain which, unfortunately, often is a source of physiologic and metabolic stress.

These problems are associated with the changes which occur in rumenal fermentation as a result of grain ingestion. As a consequence, feeding strategies must attempt to maximize forage use while not compromising nutrient supply needed for maintenance and production.

A solution to the problem of nutrient supply and demand in the ruminant animal, as imposed by the limitations of bacterial, pregastric digestion, is to enhance the efficiency and rate at which this process occurs. The rumen is a continuous fermentation system that is provided with nutrients (feeds), buffers (salivary and other salts) and fluids (water and saliva) on both a continuous and an intermittent basis. The efficiency of this fermentation is measured through rumen turnover. Turnover is conventionally expressed as the portion of the rumen contents that leaves the rumen per hour. Liquids and solids turn over at different, but usually related, rates. Liquid flow rates, as proportions of the total liquid volume, have been found to turn over at rates that increased from <8 to 13.5%/hr as dry matter intake went from 5 to 21 kg/day (*Livestock Prod. Sci.,* 17:37, 1987). At the same time, solids turnover increased from 3 to 5%/hr due to increased intake. In other studies, values of 17%/hr for liquids (*Can. J. Ani. Sci.,* 64 (Supp.):80, 1984) and as high as 7.0%/hr for concentrates (J. Dairy Sci., 65:1445, 1982) were reported. In a typical ration of a dairy cow consuming >20 kg dry matter/day, representative rumen digesta passage rates would be 15%/hr for liquids, 6%/hr for grains and 4.5%/hr for forages. The rates would all decrease with a lower level of intake.

Another important rumen characteristic associated with turnover rate is microbial yield, where microbial yield is defined as the quantity of microbial mass flowing from the rumen per day. A further, and important refinement of this expression of microbial yield, which is also effected by turnover rate, is the efficiency of microbial yield. This is usually expressed as grams of microbial protein (or nitrogen) produced per kg of organic matter (OM) digested in the rumen. Both aspects of microbial production have applied significance. Microbial yield is important as an index of the amount of microbial protein available to the ruminant animal per day. Microbial efficiency is important as part of the calculation of microbial yield where: microbial yield (gr of microbial N/day)=microbial efficiency (gr microbial N/kg digested organic matter)×kg OM digested in the rumen per day.

Because of the rapid rumen turnover rates commonly found in cattle with high dry matter intakes, such as dairy cattle, high microbial efficiencies are expected. If, however, an imbalance in the nutrients available to the rumen microbes occurs, the microbial efficiency can be impaired. This is particularly evident if ruminally available nitrogen or carbohydrate sources are inadequate.

Another factor which effects ruminal microbial efficiency and yield is predation by rumen protozoa. The rate of bacterial predation is proportional to the concentration of bacteria available. Coleman (The Roles of Protozoa and Fungi in Ruminant Digestion. Armidale, Penambul Books, 1989, p. 13) reported that when bacterial concentrations were $10^9$/ml, a value representative of that in rumen fluid, the average uptake for 18 protozoal species was 493 bacteria/hr/protozoa; when bacteria were at the maximum density, the average uptake for the 18 species of protozoa was 3,739 bacteria/hr/protozoa. Protozoal predation involves engulfment which usually kills the bacteria. The overall effect of predation on bacterial numbers is considerable.

It has been shown that the removal of protozoa (defaunation) can result in a 2-4 fold increase in numbers of rumen bacteria. The reduction in bacterial numbers is not uniform across all species. Generally, more amylolytic than cellulolytic bacteria are engulfed. It is possible, therefore to conclude that the extent and rate of digestion of various carbohydrates differs between fuanated and defuanated animals. Protozoa also have negative effects on rumen function. Because of their sequestration on large feed particles and on the rumen wall, the flow of protozoa from the rumen is less than would be predicted from their concentration in the rumen and rate of digesta flow.

Therefore, although protozoa can represent 50% of the biomass in the rumen, they contribute 20% or less to the microbial protein flowing to the duodenum. In addition, predation on bacteria causes recycling of bacterial protein in the rumen. Protozoa engulf and kill large quantities of bacteria, assimilating much of the protein from these organisms.

Since most of the protozoa remain in the rumen until they lyse, microbial protein flow from the rumen also is reduced. In vivo measurements summarized by Jounay et al (Anim. Feed Sci. Tech. 21:229, 1988) indicate that defuanation resulted in a 36% increase in grs of microbial nitrogen flowing from the rumen per kg of organic matter fermented.

An additional negative aspect of protozoa on digestive function that is important to ruminants in general, and high producing dairy cows in particular, is their engulfment and digestion of particulate feed protein. This permits protozoa to assimilate proteins of low rumen degradability which have been added to the diet as sources of by-pass protein (Hoover et al. Rumen Digestive Physiology and Microbial Ecology, West Virginia University Bulletin 708T; p 22.).

The overall effects of the presence or absence of protozoa in ruminants are not well characterized because of the difficulty in reducing their numbers in viva. Compounds which have demonstrated defuanating activity have proven too toxic to safely feed to ruminants or ineffective when fed for prolonged periods of time. Thus although the benefits of defuanation have been conclusively demonstrated in vitro, the transferal of this information to field practice has yet to be accomplished.

OBJECTS AND SUMMARY OF THE INVENTION

In view of deficiencies in the art as described above and other related goals well known in the art, one object of the present invention is to provide a feed additive method of use which, when used as a component in ruminant diets, will control, reduce and prevent protozoal populations in the ruminant by promoting facultative bacterial growth.

Another object of the present invention is to provide a feed additive and method of use which allows for the control, reduction and prevention of protozoal populations and thereby allow for the maximization of ruminal microbial growth and efficiency, the benefits of which increased flow of microbial protein to the duodenum, increased ruminal fermentation efficiency, and increased dry matter intake.

Yet another object of the invention is to provide a feed additive that does not have any negative effects upon the bacterial population of the rumen.

An exemplary embodiment of the invention provides a method for controlling, reducing or preventing the growth of protozoa in the rumen of a ruminant, comprising feeding an antiprotozoal amount of a composition comprising cell bodies of a facultative anaerobe *Corynebacterium*, or *Brevibacterium* having antiprotozoal activity, glutamic acid fermentation solubles, or corn fermentation solubles to a ruminant, and thereby promoting facultative anaerobe growth to increase the amount of said cell bodies and the fermentation solubles including such cell bodies.

The composition and compound, when used as a feed supplement in a diet formulated for ruminant animals, will significantly reduce ruminal protozoal populations, although the use of the invention to control protozoal populations is not restricted to ruminal control alone.

The method of the present invention of ruminal protozoal control has been shown to significantly enhance feed intake and increase ruminal digestive efficiency. Simply stated, the compound of the present invention includes a combination of bacterial cell bodies, nonprotein nitrogen and amino acids dried on a carrier. In a preferred embodiment of the invention the source of the antiprotozoal compound is derived from the cell bodies of facultative bacterial species, preferably~*Corynebacterium*. Another source is *Brevibacterium*. Preferred species are *lactofermentum* and *glutamicum*. Antiprotozoal activity is found in the isolated cell bodies themselves or in the byproduct materials derived from the fermentations driven by these bacteria in which the cell bodies may be present (fermentation solubles). Examples are glutamic acid fermentation solubles and corn fermentation solubles. In ruminant animals, the cell bodies and/or the fermentation byproducts may be fed unprocessed (undried), although maximum response is achieved when the cell bodies and/or the byproducts are dried at temperatures that do not denature the organic nitrogen components present therein. This temperature varies with the drying method used and generally ranges from not less than about 80 to not more than about 900 degrees Fahrenheit.

DETAILED DESCRIPTION OF THE INVENTION

The above objects have been obtained by the discovery of a method of controlling growth of protozoa in the rumin of a ruminant animal that does not have any negative effects upon the bacterial population of the rumen. The method significantly enhances feed intake and increases ruminal digestive efficiency. Simply stated, a compound of the present invention includes a combination of bacterial cell bodies, nonprotein nitrogen and amino acids dried on a carrier which is fed to the ruminant animals to promote desired bacterial growth and retard protozal growth.

One preferred embodiment of the present invention is a method for controlling, reducing or preventing the growth of protozoal bacteria in the rumen of a ruminant comprising feeding a ruminant an antiprotozoal amount of a composition comprising cell bodies of a faculative anaerobes selected from the group consisting of *Corynebacterium* cell bodies and *Brevibacterium* cell bodies or a mixture of *Corynebacterium* cell bodies and *Brevibacterium* cell bodies, glutamic acid fermention solubles, corn fermentation solubles, glutamic acid fermentation solubles and corn fermentation solubles, as will be described in greater detail as follows. The cell bodies and fermentation solubles have antiprotozoal activity when introduced to the rumen of the ruminant.

The materials employed in the method of the present invention are comprised of the liquid end streams of fermentations driven by the bacterial species *Corynebacterium* and/or *Brevibacterium*. These end streams may be characterized as being about 40% solids in composition. The solids are comprised of nonprotein nitrogen, peptides, and amino acids and any residual unspent carbohydrate remaining from the fermentation.

The predominant source of both the peptides and amino acids is the lysed cell bodies of the facultative bacterial species already referenced which result from the fermentation driven by the bacteria.

The antiprotozoal compound is derived from the cell bodies of facultative bacterial species, preferably~*Corynebacterium*. Another source is *Brevibacterium*. Preferred species are *lactofermentum* and *glutamicum*. Antiprotozoal activity is found in the isolated cell bodies themselves or in the byproduct materials derived from the fermentations driven by these bacteria in which the cell bodies may be present (fermentation solubles). Examples are glutamic acid fermentation solubles and corn fermentation solubles In the preferred embodiment of the invention, this composition is obtained from either glutamic acid fermentation solubles, corn fermentation solubles or a mixture thereof or the isolated cell bodies themselves, although any fermentation end stream possessing these components and derived from fermentations driven by the bacterial species *Corynebacterium* and/or *Brevibacterium* may be used. This composition can then be dried or left in liquid form. If dried, drying should occur at temperatures that will not denature the organic components of the composition. A carrier such as wheat middlings etc. can be included if desired and in view of the drying method used. Any amount of carrier may be used. Typical ranges (wt/wt) of dried solubles to wheat middlings are from 10 to 1 to 1 to 10 including all values and subranges therebetween. The carrier is preferably edible by the ruminant and is preferably a common feed ingredient. Either of these solubles or the isolated cell bodies alone or individually, blended onto a carrier, if necessary, are suitable.

When the corn and glutamic acid fermentation solubles are mixed, or the solubles and the isolated cell bodies are mixed, they are mixed in any proportion, either before or after drying and each optionally on a carrier, if mixed dry. The compositions described in U.S. Pat. No. 5,709,894, which is incorporated herein by reference, may also be used herein.

The one or more solubles and cell bodies if dried, are brought to a moisture content of about 30% at a low temperature. Moisture contents of 0%, 8%, 14% or the like also are acceptable. Drying methods which may be used include vacuum drying, direct and indirect heat application, spray drying, evaporation, etc.

A forced air grain processor otherwise useful to roast soybeans is preferred for the solubles or blends of the solubles, or blends of the solubles and isolated cell bodies. Vacuum drying is preferred for the cell bodies alone. Regardless of the method used, drying must be done at temperatures which will not denature the nitrogen fractions.

*Corynebacterium* and *Brevibacterium* are facultative anaerobes used in a number of industrial fermentation processes. Examples are the production of amino acids such as lysine (*Brevibacterium ilium*) and glutamic acid (*Corynebacterium ilium; Corynebacteria glutamicum*). It is the opinion of some taxonomists that *Cornyeabacterium* and *Brevibacterium* are the same organism however and the current distinction comes from improvements in classification techniques. The end streams of the fermentations driven by these organisms typically are liquid effluents having greater than 30 wt % water (moisture), typically 50-60%. They commonly contain nonprotein nitrogen, peptides and amino acids largely derived from the lysed cell bodies of the referenced organisms and may contain small amounts of residual carbohydrates remaining from the fermentations themselves. Examples are Glutamic Acid Fermentation Solubles and Corn Fermentation Solubles.

The culture of these organisms and their industrial use for the production of amino acids are a well known and common manufacturing process, and the nomenclature for the end streams are defined as has been determined by the Association of American Feed Control Officials. Glutamic Acid Fermentation Solubles is comprised of a combination of water, nonprotein nitrogen, primarily in the form of ammonium chloride, peptides and free amino acids derived primarily from the hydrolysis of the microorganisms used to produce the fermentation, glutamic acid and inorganic salts such as $MgSO_4$, NaCl and $KH_2PO_4$. Corn Fermentation Solubles is comprised of a combination of water, nonprotein nitrogen, primarily in the form of ammonium sulfate, peptides and free amino acids derived from the hydrolysis of the microorganisms used to produce the fermentation and the inorganic salts such as $MgSO_4$, NaCl, and $MnSO_4$. The isolated cell bodies of the bacteria are comprised of primarily peptides, and free amino acids, although some nonprotein nitrogen may be present as an artifact.

By introducing the compound to the rumen of the animal, fermentation is enhanced, consequently resulting in additional fermentation solubles as well as increased numbers of faculatative bacterial cell bodies. Therefore, the invention is useful as a feed additive in any ruminant diet. The compound when fed to ruminant animals, significantly reduces ruminal protozoal populations (numbers). The reduction in protozoal population can be 100%, 95%, 90%, 85%, 75%, 65%, 50%, 25%, 10% and 5% or lower, depending upon dosage and feeding schedule. The net result even at low % reductions of protozoa is a significant increase in resident ruminal bacterial populations. It is understood, therefore, that feeding the compound of the present invention increases the beneficial ruminal bacterial population while reducing the protozoal population.

This allows for enhanced microbial fermentation efficiency, enhanced ruminal microbial yield; increased delivery of microbial protein to the duodenum and increased rumen turnover of ingested feedstuffs.

The invention feed supplement may be added to any feed fed to ruminants, preferably to feeds comprising at least one of grass, legume, corn or small grain silage or hay, grain byproducts, oilseeds and oilseed meals, corn grain, and small grains etc., to provide a supplemented feed. The amount added will generally range from 0.50 grams to 250 grams of the isolated cell bodies alone, and 250 grams to 1 kg of the solubles or blends of the soluble or blends of the solubles and isolated cell bodies per head per day, depending upon species to be fed.

The above objects are also met by a composition comprised of dried free amino acids, peptides, organic and inorganic nitrogen as well as structural (fibre) and nonstructural carbohydrates as needed. In the preferred embodiment of the invention, this composition is obtained from either glutamic acid fermentation solubles, corn fermentation solubles or a mixture thereof, although any source material that provides the components of these fermentation solubles may be used. The origin of the base materials is not important. That they provide the components of corn and/or glutamic acid fermentation solubles is. A carrier such as wheat middlings can be included if desired and in view of the drying method used. Either of these solubles alone or individually, blended onto a carrier if necessary, are suitable. When the corn and glutamic acid fermentation solubles are mixed, they are mixed in any proportion, either before or after drying and each optionally on a carrier if mixed dry.

The invention solubles (mixture or otherwise) is dried to a maximum moisture content of about 30% at low temperature. Moisture contents of 0%, 8%, 14%, etc. are acceptable. Drying methods which may be used include vacuum drying, direct and indirect heat application, spray drying, evaporation, etc. A forced air grain processor otherwise useful to roast soybeans is preferred. Regardless of the method used, drying must be done at temperatures which will allow for modification of the solubility of the nitrogen fractions without denaturing them. To the at least one of corn or glutamic acid fermentation solubles, one or a combination of cellulytic and/or amyalytic enzymes of either bacterial or fungal origin and an amino acid such as glutaminic acid may also be added to enhance biological effect. Glutamine can be used as a substitute for, or along with, glutamic acid. These materials may be added either before or after drying. Generally these components total from about 4 to about 10% by weight of the final composition. Preferred amounts of enzyme range from 15-60 gms (2% to 4%) of xylanase (75,000 xylanase units per gram) and 20 cellulose (100,000 endocellulose units per ml). Preferred amounts of glutamic acid range from 0.70 to 4.0 grs (0.07 to 0.02).

The present inventor has provided a blended source of organic and inorganic nitrogen of variable solubilities in the form of nonprotein nitrogen, peptides, amino acids and intact protein derived in the preferred embodiment of the invention from glutamic acid fermentation solubles and/or corn fermentation solubles to which a carrier, additional amino acids and enzymes can be added and which is superior to prior art compositions.

Glutamic acid fermentation solubles and corn fermentation solubles are the liquid effluents from the bacterial fermentative process used to produce monosodium glutamate and lysine hydrochloride, respectively.

These processes are well known and common manufacturing process, and the nomenclature by which these products are defined has been determined by the Association of American Feed Control Officials.

Glutamic Acid Fermentation Solubles is comprised of a combination of water, nonprotein nitrogen, primarily in the form of ammonium chloride, peptides and free amino acids derived from the hydrolysis of the microorganisms used to produce the fermentation, glutamic acid and inorganic salts such as $MgSO_4$, NaCl and $KH_2PO_4$. Corn Fermentation Solubles is comprised of a combination of water, nonprotein nitrogen, primarily in the form of ammonium sulfate, peptides and free amino acids derived from the hydrolysis of the microorganisms used to produce the fermentation and inorganic salts such as $MgSO_4$, NaCl, and $MnSO_4$.

Any enzyme capable of reducing plant tissue such as proteins, starches, sugars, pectins, cellulose, hemicellulose, and lignin, are suitable for use in this invention. Examples of such enzymes are proteases, amylases, dextranases, pectinases, cellulases, xylanases, mannanases and ligninases. These can be either of bacterial or fungal origin. Mixtures may be used.

Any amino acid may be added to the invention mixture described above, although glutamic acid is used in the preferred embodiment of this invention.

The invention is also useful as a feed additive in any ruminant diet.

As a result of processing (i.e. drying to a moisture content of up to about 30% by weight, optionally on a carrier), the nonprotein nitrogen fractions of the invention composition, normally highly soluble in the rumen environment, are reduced in their solubility so as to provide rumen bacteria with a sustained release source of ammonia nitrogen.

The nonprotein nitrogen components are further complemented by the peptides and intact protein the invention composition provides, the net result being a feed additive which provides a nitrogen steady state which significantly enhances rumen microbial efficiency and microbial yield. That is, the composition stimulates facultative anaerobe growth of rumen bacteria. This effect can be further enhanced by the addition of an amino acid like glutamic acid which, when added to the invention composition, will supply the animal with the amino acid such as glutamic acid at a rate not less than 0.08 grams/kg of dry matter intake per day.

The addition of one or more of proteolytic, amyalytic and cellulytic enzymes also enhances the net response by allowing for the synchronization of the nitrogen sources with carbohydrates, thus ensuring the availability of sufficient quantities of energy for the increased microbial protein synthesis that is stimulated by the modified nitrogen fractions.

The invention feed supplement may be added to any feed fed to ruminants, preferably to feeds comprising at least one of grass, legume, corn or small grain silage or hay, grain byproducts, oilseeds and oilseed meals, corn grain, and small grains etc., to provide a supplemented feed. The amount added when used as a feed additive will generally range from about 0.5 to about 12 lbs per head per day, depending upon application and species to be fed.

Having generally described this invention, a further understanding can be obtained by reference to certain specific examples which are provided herein for purposes of illustration only and are not intended to be limiting. The continuous fermentation techniques used in the experiments will not support protozoal cultures, thus responses reported are bacterial.

EXAMPLES

Preparation of the Ruminant Feed Supplement

In this example, the drying method used is forced air, although any process which allows for the removal of excess moisture while not damaging the biological value of the nitrogen components of the invention can be used, with the necessary modifications in materials preparation as dictated by the method used.

Examples

Preparation of the Ruminant Feed Supplement in a Dried Form

Although the feed supplement may be used in its unprocessed liquid form, in this example the feed supplement is prepared using a blend of glutamic acid fermentation solubles and corn fermentation solubles which is dried on a carrier, using forced air, although any process which allows for the removal of excess moisture while not damaging the product may be employed.

Preparation of the Ruminant Feed Supplement from Isolated Cell Bodies

In this example the feed supplement is prepared from isolated bacterial cell bodies. The end streams of the fermentations driven by the referenced bacteria are centrifuged at speeds which allow for adequate separation of the various phases based upon specific gravity and density. Other methods that are applicable include but are not restricted to evaporation, membrane filtration, diffusion, ion exchange, and precipitation. The cell bodies or cell cream is then dried using any method which will not denature the nitrogen fractions present.

The Effect of the Ruminant Feed Additive on Ruminal Protozoal Populations as Measured by the In Vitro Breakdown of ($^{14}$C) leucine-labeled *Selenomonas ruminatium*

Example 1

A series of in vitro experiments were conducted to determine the antiprotozoal activity of the ruminant feed additive using the a method as described by Wallace and McPherson (British Journal of Nutrition 58, 313-323) and Wallace and Newbold (Journal of Agricultural Science, Cambridge, 116, 163-168). In this method, protozoal activity 25 is measured by the breakdown of (14C) leucine-labeled *Selenomona ruminantium.*

Rumen fluid, collected from mature rumen cannulated sheep is strained through 2 layers of muslin and pre-incubated at 39° C. with a mixture (40 g/L) of the invention feed additive with wheat straw (0, 1, 10, 25, and 50 grams of the invention feed additive) for 2 hr. before adding the *S. ruminantium.*

Unlabeled L-leucine was included in all incubations at a final concentration of 5 mmol/L to prevent reincorporation of released ($^{14}C$) leucine.

In this experiment, the invention feed additive was a blend of liquid glutamic acid fermentation solubles and corn fermentation solubles mixed at a 60/40 weight/weight ratio, dried on a wheat midds carrier on a 50/50 weight basis. Drying method used was forced air.

The results of this experiment are summarized in Table 1. As the concentration of the invention feed additive increased from 1 gram per liter to 50 grams per liter, the breakdown of S. ruminantium as a result of protozoal predation, and measured as percent breakdown per hour, decreased linearly from 6.21% as measured in the control, to 0.98% when the concentration of the invention feed additive reached 50 grams/liter.

As can be seen in this dramatic and significant response to the invention feed additive, protozoal predation of the bacteria, S. ruminantium, which is widely known by practitioners of the art to be a direct function of ruminal protozoal population concentrations was reduced to levels of less than 1% per hour when the invention feed additive was incorporated into the culture media.

Example 2

These experiments used the method of Wallace et. al. and measured the antiprotozoal activity of: (a) a 60/40 combination of liquid glutamic acid fermentation solubles and 5 corn fermentation solubles dried on a wheat midds carrier (50/50 weight/weight basis), using the forced air method as described above, but then made into an aqueous solution to give an equivalent concentration of 10 grams of dry material per liter; (b) glutamic acid fermentation solubles or corn fermentation solubles in liquid form alone; (c) the preparation as in (a) but autoclaved; (d) the preparation as in (a) but ashed; (e) the preparation as in (a) but subjected to dialysis for 24 hr.

The results of these experiments are summarized in tables 2 and 3. As can be seen in these data, the antiprotozoal activity of the invention feed additive is similar to that reported for a comparable dilution in Table 1, with the exception of the ashed and autoclaved samples, where the biological activity of the invention is destroyed, as indicated by a lack of a significant response over the control. In the dialyzed sample, the invention's antiprotozoal activity was unaffected, indicating the biological agent is either water insoluble or larger than 10,000 molecular weight. Finally the antiprotozoal activity of the invention feed additive is similar regardless of whether the source is a blend of the fermentation solubles or either one alone. An additional experiment using the same methods but measuring the antiprotozoal activity of cell bodies of *C. glutamicum* isolated from the glutamic acid fermentation solubles, demonstrated antiprotozoal activity comparable to that of the dried glutamic acid fermentation solubles alone, thus indicating that the active agent is most likely a component of the cell cream itself, as no antiprotozoal activity was found in the wheat middlings carrier.

The Effects of Feeding the Invention Feed Additive on Numbers of Rumen Protozoa in Lactating Dairy Cattle Soybean meal was used as the main protein source in a control (C) diet for lactating dairy cows. In the experimental diet, 100% of the soybean meal (9.6 lbs) was replaced with a comparable amount of the invention feed additive, in this case, a 60/40 wgt/wgt blend of glutamic acid fermentation solubles and corn fermentation solubles dried on a wheat midds carrier using the forced air method as previously described. Two lactating dairy cows, fitted with rumen cannulae were fed diet (C) for a two week period, then switched to the experimental diet. During the second week on each diet, rumen contents were removed from each cow and protozoal numbers were determined according to the procedure of Abe and Kumeno (J. Animal Sci. 36:941. 1973). The results of this experiment are summarized in table 3. As can be seen, the feed additive invention reduced protozoal numbers by an average of 66% over those observed when the animals were consuming the control diet. These data confirm the previously reported in vitro observations and verify the value of the feed additive under field conditions in controlling protozoal numbers in vivo.

TABLE 1

The Effect of the Feed Additive on Protozoal Activity as Determined by Its Effect on the Breakdown of *Seleneomonas ruminantium* in Rumen Fluid.

| Feed Additive Concentration (gr/l) | Breakdown of *S. ruminantium* (%/hr) |
|---|---|
| Control (no feed additive present) | 6.21 |
| 1 gr/l | 5.24 |
| 10 gr/l | 3.70 |
| 25 gr/l | 1.54 |
| 50 gr/l | 0.98 |

TABLE 2

The Effects of Processing on Efficacy of the Feed Additive After Dilution to 10 gr/l.

| Physical Form | Breakdown of *S. ruminantium* (%/hr) |
|---|---|
| Control (no feed additive present) | 6.86 |
| Diluted to 10 gr/l | 3.30 |
| Diluted and Autoclaved | 6.02 |
| Diluted and Ashed | 5.60 |
| Diluted and Dialyzed | 3.61 |

TABLE 3

A Comparison of the Feed Additive as Prepared from 5 either Liquid Glutamic Acid Fermentation Solubles or Corn Fermentation Solubles Vs a Control and Wheat middlings on Protozoal Activity as Determined by Its Effect on the Breakdown of *Selenomonas ruminantium* in Rumen Fluid.

| Source | Breakdown of *S. ruminantium* (%/hr) |
|---|---|
| Control | 7.02 |
| Wheat Midds | 7.06 |
| Glutamic Acid Solubles (lOO ml/l) | 4.59 |
| Corn Fermentation Solubles (lOO ml/1) | 3.58 |

TABLE 4

The Effect of the Feed Additive on Protozoa Numbers When Used as a Dietary Component in Lactating Dairy Cattle

| | Total Protozoa/ml of Rumen Contents | |
|---|---|---|
| Cow No. | Control | Feed Additive |
| 1 | $6.8 \times 10^5$ | $2.9 \times 10^5$ |
| 2 | $7.4 \times 10^5$ | $1.8 \times 10^5$ |
| Average | $7.1 \times 10^5$ | $2.4 \times 10^5$ |

The average decrease in protozoa numbers due to the presence of the feed additive was 66%.

It will be appreciated that as the protozoa population was reduced, so was the breakdown of *S. ruminantium*. Therefore, by increasing the concentration of the additive of the present invention, the antiprotozoal activity was increased. The examples demonstrate that the compound of the present invention has pronounced antiprotozoal effect, which is dose related. As explained above, an experiment using the same methods but measuring the antiprotozoal activity of cell bodies of *C. glutamicum* isolated from the glutamic acid fermentation solubles, demonstrated antiprotozoal activity comparable to that of the dried glutamic acid fermentation solubles alone, indicating that the active agent is most likely a component of the cell cream itself i.e. cell bodies, as no antiprotozoal activity was found in the wheat middlings carrier.

As used herein, controlling, reducing and preventing "antiprotozoal amounts" of the invention composition or compound are those amounts which decrease protozoa numbers present in the rumen, which prevent further growth, and which prevent growth where no protozoa are present, respectively.

What is claimed is:

1. A method for decreasing protozoa numbers present in a rumen of a ruminant, comprising feeding an antiprotozoal amount of a composition to a ruminant comprising a mixture of a) whole cells of facultative anaerobe *Corynebacterium glutamicum*, b) glutamic acid fermentation solubles and corn fermentation solubles.

2. The method according to claim 1, wherein said composition further comprises a carrier, and wherein said carrier is wheat middlings.

* * * * *